(12) United States Patent
Sprain et al.

(10) Patent No.: US 7,803,014 B2
(45) Date of Patent: Sep. 28, 2010

(54) IMPLANTABLE MEDICAL DEVICE ASSEMBLY AND MANUFACTURING METHOD

(75) Inventors: Jason W. Sprain, Shoreview, MN (US); Anthony Joseph Angelo, Forest Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 11/278,051

(22) Filed: Mar. 30, 2006

(65) Prior Publication Data

US 2007/0232119 A1    Oct. 4, 2007

(51) Int. Cl.
*H05K 1/00* (2006.01)

(52) U.S. Cl. .................. 439/526; 439/909; 607/9

(58) Field of Classification Search .......... 439/357, 439/525–526, 909; 607/2, 36–37, 9; 361/309, 361/302–304, 307, 752
See application file for complete search history.

(56) References Cited

U.S. PATENT DOCUMENTS

| 4,352,951 | A |   | 10/1982 | Kyle |
|---|---|---|---|---|
| 4,399,819 | A |   | 8/1983 | Cowdery |
| 5,660,177 | A |   | 8/1997 | Faupel et al. |
| 5,679,026 | A |   | 10/1997 | Fain et al. |
| 5,755,743 | A |   | 5/1998 | Volz et al. |
| 5,759,197 | A |   | 6/1998 | Sawchuk et al. |
| 5,871,515 | A |   | 2/1999 | Wiklund et al. |
| 5,942,842 | A |   | 8/1999 | Fogle |
| 5,951,595 | A |   | 9/1999 | Moberg et al. |
| 6,026,325 | A | * | 2/2000 | Weinberg et al. ............ 607/36 |
| 6,044,302 | A |   | 3/2000 | Persuitti et al. |
| 6,052,623 | A | * | 4/2000 | Fenner et al. ............ 607/36 |
| 6,205,358 | B1 |   | 3/2001 | Haeg et al. |
| 6,414,835 | B1 |   | 7/2002 | Wolf et al. |
| 6,428,368 | B1 |   | 8/2002 | Hawkins et al. |
| 6,456,256 | B1 |   | 9/2002 | Amundson et al. |
| 6,459,935 | B1 |   | 10/2002 | Piersma |
| 6,519,133 | B1 |   | 2/2003 | Eck et al. |
| 6,566,978 | B2 |   | 5/2003 | Stevenson et al. |
| 6,622,046 | B2 |   | 9/2003 | Fraley et al. |
| 6,765,780 | B2 |   | 7/2004 | Brendel et al. |
| 6,817,905 | B2 |   | 11/2004 | Zart et al. |
| 6,882,248 | B2 |   | 4/2005 | Stevenson et al. |

(Continued)

FOREIGN PATENT DOCUMENTS

EP    0405838 A2    1/1991

(Continued)

OTHER PUBLICATIONS

"PCT Application No. PCT/US2007/063749, International Search Report mailed Sep. 27, 2007", 4 pgs.

(Continued)

*Primary Examiner*—Edwin A. Leon
(74) *Attorney, Agent, or Firm*—Schwegman, Lundberg & Woessner, P.A.

(57) ABSTRACT

An implantable device includes a housing, a circuit board having a plurality of through holes, and a plurality of interconnect pins within the housing and oriented perpendicular to a major surface of the housing. The circuit board is connected to the interconnect pins such that the pins extend through the through holes of the circuit board.

23 Claims, 4 Drawing Sheets

U.S. PATENT DOCUMENTS

| | | | |
|---|---|---|---|
| 7,035,077 B2 * | 4/2006 | Brendel | 361/302 |
| 7,108,711 B2 | 9/2006 | Vogel et al. | |
| 7,274,963 B2 | 9/2007 | Spadgenske | |
| 2002/0027484 A1 | 3/2002 | Stevenson et al. | |
| 2003/0040780 A1 | 2/2003 | Haeg et al. | |
| 2003/0139096 A1 | 7/2003 | Stevenson et al. | |
| 2004/0012462 A1 | 1/2004 | Kim | |
| 2004/0078062 A1 | 4/2004 | Spadgenske et al. | |
| 2004/0116976 A1 | 6/2004 | Spadgenske | |
| 2004/0215280 A1 | 10/2004 | Dublin et al. | |
| 2004/0215281 A1 | 10/2004 | O'Phelan et al. | |
| 2005/0060003 A1 | 3/2005 | Taylor et al. | |
| 2005/0247475 A1 | 11/2005 | Stevenson et al. | |
| 2006/0282126 A1 * | 12/2006 | Fischbach et al. | 607/37 |
| 2007/0239222 A1 | 10/2007 | Sprain et al. | |

FOREIGN PATENT DOCUMENTS

| | | |
|---|---|---|
| EP | 0916364 A2 | 5/1999 |
| GB | 2127629 | 4/1984 |
| WO | WO-03073450 A1 | 9/2003 |
| WO | WO-2004105572 A2 | 12/2004 |
| WO | WO-2007114993 A2 | 10/2007 |
| WO | WO-2007114993 A3 | 10/2007 |
| WO | WO-2007117812 A2 | 10/2007 |
| WO | WO-2007117812 A3 | 10/2007 |

OTHER PUBLICATIONS

"PCT Application No. PCT/US2007/063749, Written Opinion mailed Sep. 27, 2007", 7 pgs.

"PCT Application No. PCT/US2007/063897, International Search Report mailed Oct. 17, 2007", 4 pgs.

"PCT Application No. PCT/US2007/063897, Written Opinion mailed Oct. 17, 2007", 6 pgs.

"U.S. Appl. No. 11/278,047, Non-Final Office Action mailed May 27, 2008", 10 pgs.

"U.S. Appl. No. 11/278,047, Response filed Aug. 27, 2008 to Non Final Office Action mailed May 27, 2008", 8 pgs.

"U.S. Appl. No. 11/278,047 Final Office Action mailed on Dec. 11, 2008", 7 pgs.

"U.S. Appl. No. 11/278,047, Pre-Appeal Brief Request mailed Mar. 3, 2009", 4 pgs.

"U.S. Appl. No. 11/278,047, Response filed Feb. 11, 2009 to Final Office Action mailed Dec. 11, 2008", 9 pgs.

"U.S. Appl. No. 11/278,047, Advisory Action mailed Mar. 3, 2009", 3 pgs.

"U.S. Appl. No. 11/278,047, Final Office Action mailed Jul. 24, 2009", 7 pgs.

"U.S. Appl. 11/278,047, Pre-Appeal Brief Request filed Sep. 23, 2009", 5 pgs.

"U.S. Appl. No. 11/278,047, Non-Final Office Action mailed Jan. 19, 2010", 7 Pgs.

"U.S. Appl. No. 11/278,047, Response filed Apr. 19, 2010 to Non Final Office Action mailed Jan. 19, 2010", 9 pgs.

* cited by examiner

IMPLANTABLE MEDICAL DEVICE ASSEMBLY AND MANUFACTURING METHOD

FIELD OF INVENTION

This invention relates to the field of implantable devices and more specifically to an implantable medical device.

BACKGROUND

Implantable medical devices are used to treat many conditions. Implantable medical devices can include pulse generators, such as pacemakers and defibrillators, which include electronics mounted within a housing. The housing includes a header which is typically connected to a lead, which is implanted on or in the heart.

An electrical feedthrough on the housing connects internal electronics to the lead via the header connection. The feedthrough is usually mounted to the housing and a connector is attached to a contact of the internal electronics and then routed to and attached to the feedthrough. There is a need for less complex manufacturing and more mechanically and electrically robust connections between the internal electronics of the housing and the feedthrough.

SUMMARY

In one embodiment, an implantable device includes a housing, a circuit board having a plurality of through holes, and a plurality of interconnect pins within the housing, each of the interconnect pins including a straight shaft oriented perpendicular to a major surface of the housing. The circuit board is connected to the interconnect pins such that the pins extend through the through holes of the circuit board.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1:
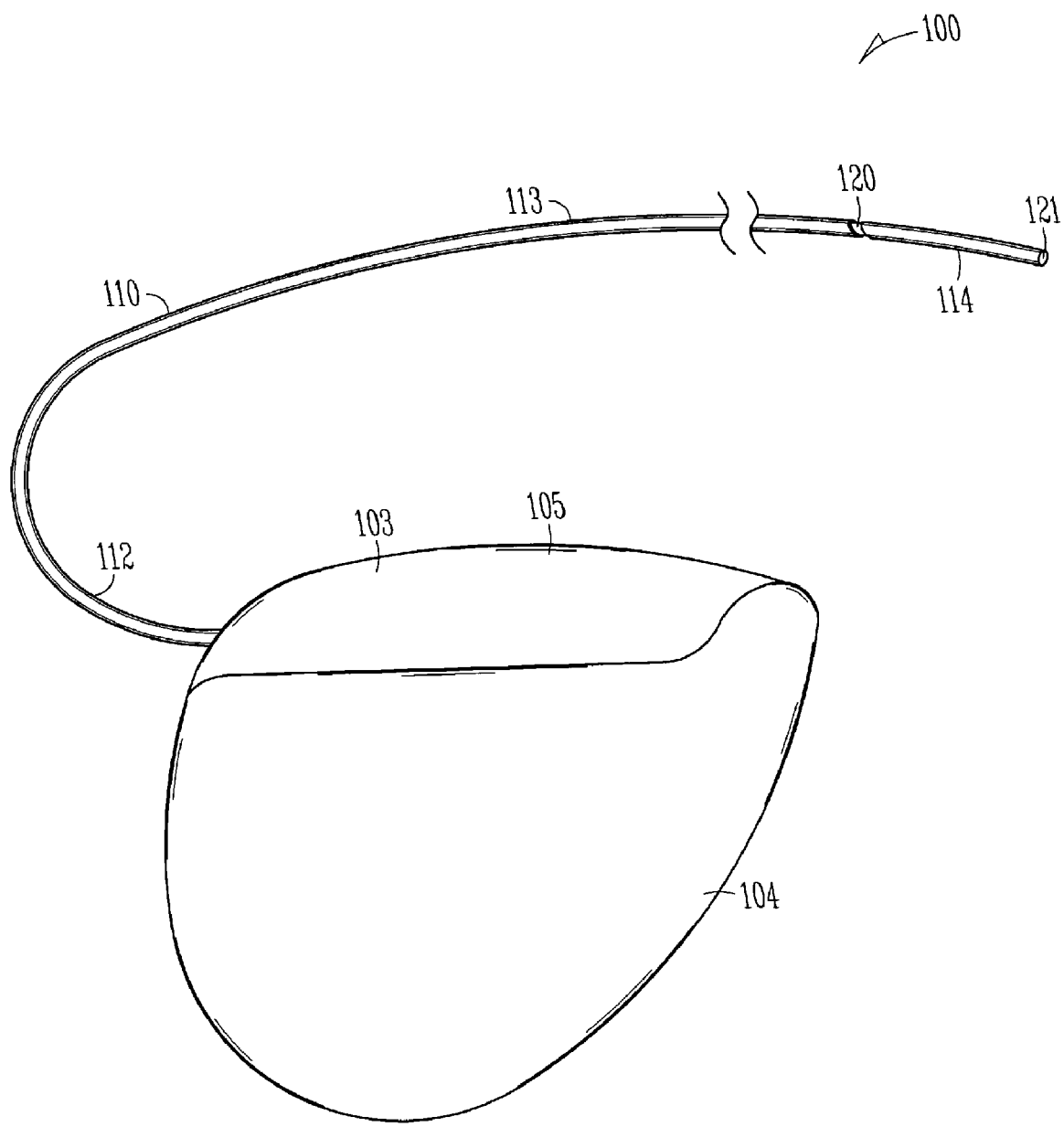
FIG. 1 shows a view of an implantable system according to at least one embodiment.

FIG. 1 shows an implantable system 100, in accordance with one embodiment. System 100 includes an electronics unit, such as a pulse generator 105, and at least one lead 110. The pulse generator 105 includes a hermetically sealed pulse generator housing 104 and a header 103. The pulse generator 105 is generally implanted into a subcutaneous pocket made in the wall of the chest. Alternatively, the pulse generator 105 is placed in a subcutaneous or submuscular pocket made in the abdomen, or in other locations. Pulse generator 105 can include a power supply such as a battery, a capacitor, and other components housed in a case. The device can include one or more microprocessors to provide processing, evaluation, and to determine and deliver electrical shocks and pulses of different energy levels and timing for defibrillation, cardioversion, and pacing to a heart in response to cardiac arrhythmia including fibrillation, tachycardia, heart failure, and bradycardia.

Lead 110 includes a lead body 113 having a proximal end 112, where the lead is coupled at the header 103 of pulse generator 105. The lead 110 extends to a distal end 114, which is coupled with a portion of a heart, when implanted. In one embodiment, the distal end 114 of the lead 110 includes one or more electrodes 120, 121 which electrically couple the lead 110 with a heart. In other examples, electrodes can be located medially or at other locations along the lead. At least one electrical conductor is disposed within the lead 110 and extends from the proximal end 112 to the electrode(s) 120, 121. The electrical conductors carry electrical current and pulses between the pulse generator 105 and the electrode(s) 120, 121.

In other embodiments, system 100 is suitable for use with implantable electrical devices, such as, but not limited to, pulse generators, neuro-stimulators, skeletal stimulators, central nervous system stimulators, or stimulators for the treatment of pain. The system can also be utilized as a sensor and/or a receiver. The electrodes can be used, for sensing, pacing, and/or shocking, for example.

Figure 2:
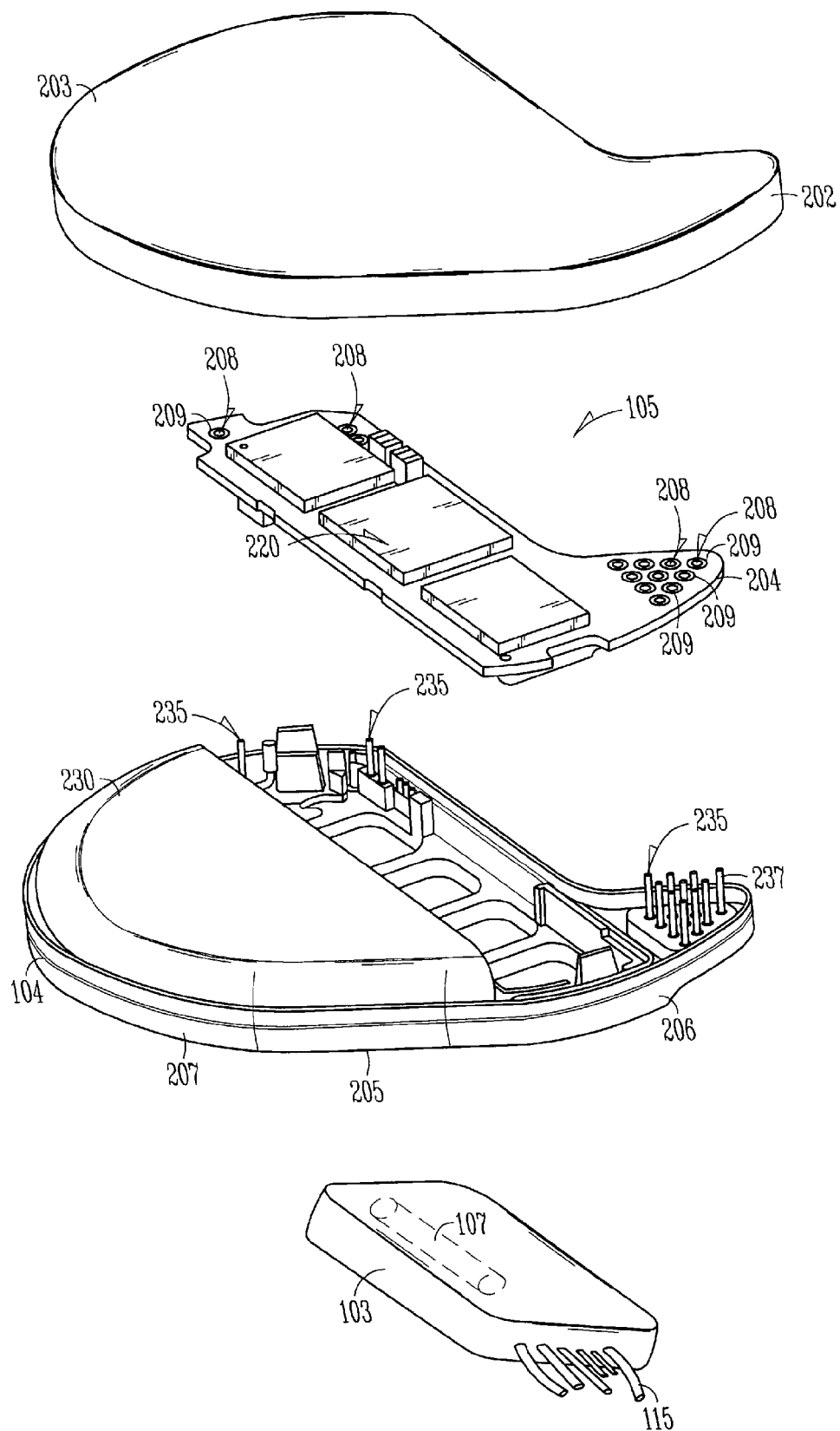
FIG. 2 shows an exploded view of a portion of the implantable device of FIG. 1.
Figure 3:
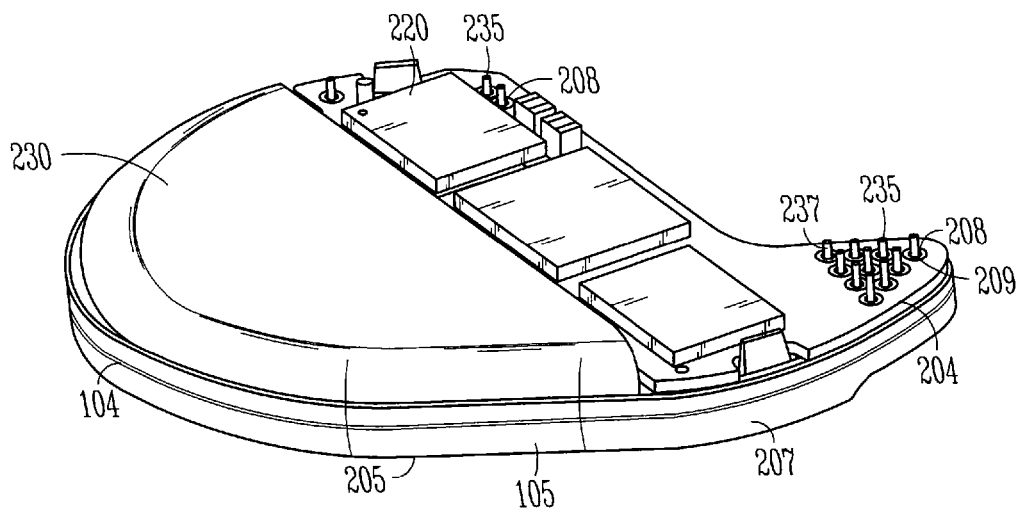
FIG. 3 shows a perspective view of a portion of the implantable device of FIG. 1.
Figure 4:
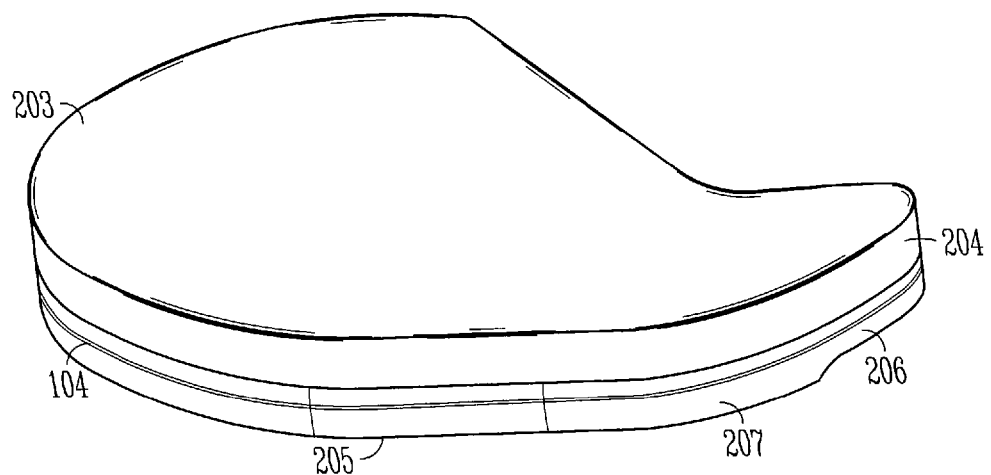
FIG. 4 shows a perspective view of a portion of the implantable device of FIG. 1.

FIGS. 2-4 show further details of pulse generator 105, in accordance with one embodiment. FIG. 2 shows an exploded view of a portion of pulse generator 105, in accordance with one embodiment. FIG. 3 shows a circuit board 204 mounted to pulse generator housing 104, and FIG. 4 shows housing 104, in accordance with one embodiment.

Housing 104 includes an electrical enclosure for holding electrical components 220, including battery 230, and includes a top portion 202 and a bottom portion 206. Top portion 202 includes a top surface 203 and bottom portion 206 includes a bottom surface 205. After the top portion 202 and the bottom portion 206 are connected together, by laser welding, for example, top surface 203 and bottom surface 205 are generally parallel to each other and separated by a side wall 207 extending around the periphery of the housing 104.

In this example, pulse generator 105 includes a battery 230 and a hybrid or other circuit board 204 having electrical components 220 mounted thereon. Components 220 can be mounted to either side or to both sides of the circuit board 204. Circuit board 204 can include a rigid circuit board or a flex circuit board. Electrical components 220 can include microprocessors and other components for controlling the functions of the pulse generator 105. In one embodiment, circuit board 204 also includes a plurality of through holes 208. Through holes 208 extend through the entire body of the circuit board 204. Positioned near or surrounding through holes 208 are electrical contacts 209. Particular electrical contacts 209 are typically electrically connected to particular other contacts 209 or to particular components 220 on the circuit board.

Within the housing 104 are a plurality of interconnect pins 235. One or more of the plurality of interconnect pins 235 include an electrically conductive straight shaft that is oriented so that the longitudinal axis of the shaft is perpendicular to top and bottom surfaces 203, 205. In various examples, interconnect pins 235 provide electrical connection between the battery 230 and circuit board 204, or between the circuit board 204 and header 103, or between different electrical components 220 on the circuit board 204 itself, or between electrical components 220 and a receiver or an antenna outside the housing 104, for example.

Figure 5:
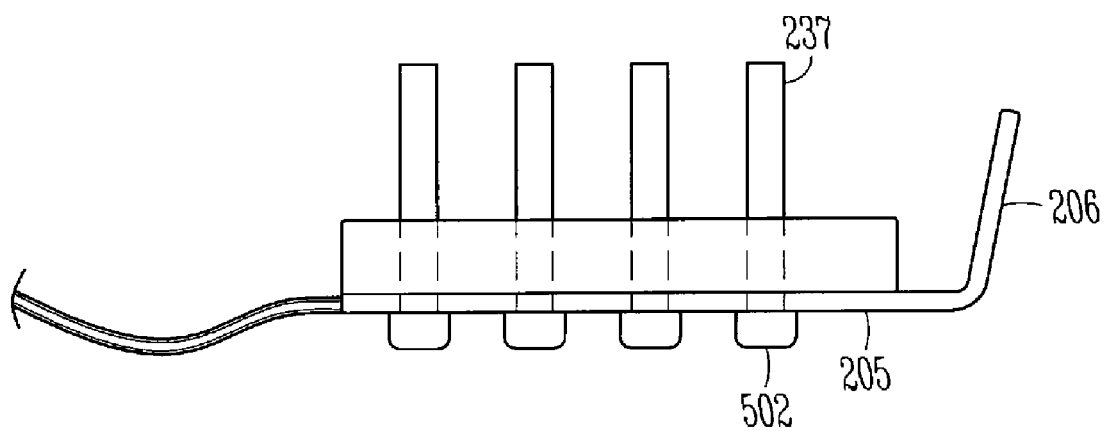
FIG. 5 shows a cross-section view of interconnect pins, in accordance with one embodiment.

In this example, interconnect pins 235 include feedthrough pins 237. Feedthrough pins 237 include straight, electrically conductive shafts and are electrically insulated from housing 104 and extend through housing 104 to an outer surface of the housing so as to provide communication with header 103. Referring to FIG. 5, at least one of the feedthrough pins 237 is oriented such that an outer connection surface 502 of the feedthrough pin lies in a parallel plane to the major surface 205 of bottom portion 206 of housing 104.

Referring again to FIG. 2, feedthrough pins 237 are connectable to connectors 115 of the header 103. In this example, header 103 includes one or more longitudinal bores 107 that are configured to receive a lead terminal of lead 110 (FIG. 1). The lead terminal can include one or more contacts to contact corresponding contacts within the header. The header contacts are electrically connected to the electronics in pulse generator housing 104 via connectors 115 which in turn connect to feedthrough pins 237. For example, each of connectors 115 can be aligned with one or more of feedthrough pins 237 and then are connected to connection surface 502 (FIG. 5) of the feedthrough pins 237.

Referring to FIG. 3, circuit board 204 is mounted into the pulse generator housing 104 such that the circuit board's major surface is parallel to the top surface 203 and bottom surface 205. When the circuit board 204 is mounted within housing 104, the interconnect pins 235 extend through the through holes 208 of the circuit board and contact the contacts 209.

This system allows for less complex manufacturing than past implantable devices. Interconnect pins 235 are located within housing 104 in a predetermined configuration and the through holes 208 have a matching configuration. Accordingly, by simply placing the circuit board 204 onto the interconnect pins 235, and then performing a final connection, if necessary, the circuit board 204 is physically mounted to the housing and electrically coupled to other components of the system such as electrodes 120, 121 (FIG. 1). For example, the contacts 209 and interconnect pins 235 can be coupled by welding, brazing, soldering, a friction connection, conductive epoxy, or other technique. Moreover, a direct connection between connector pins 235 and circuit board 204 eliminates the need for separately routed wire connectors between the circuit board and other components. Also, the circuit board 204 is positioned over the interconnect pins 235 without the need for manipulation or reorientation of the interconnect pins or bending of the circuit board. This reduces fixturing equipment and investment and other costs related to manufacturing.

Figure 6:
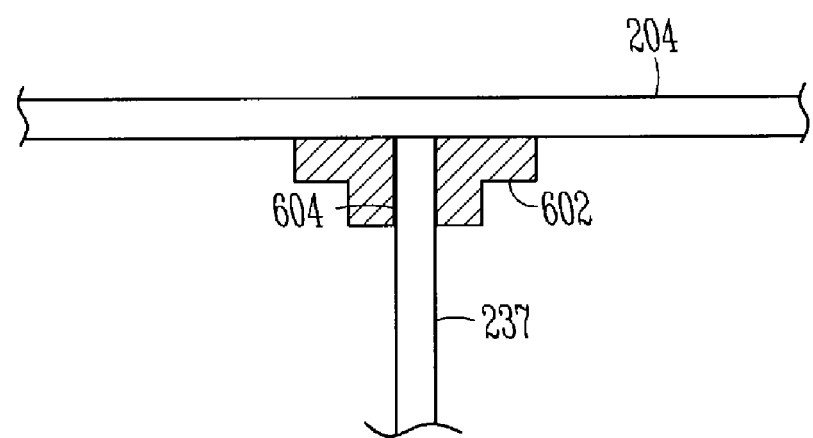
FIG. 6 shows a side view of a connection between a circuit board and an interconnect pin, in accordance with one embodiment.

FIG. 6 shows a side view of a connection between a circuit board 204 and an interconnect pin 237, in accordance with one embodiment. In this example, the contact 602 of circuit board 204 includes a friction-fit contact 604. Interconnect pin 237 fits within contact 604 to make the connection. In other examples, the pin 237 can further be soldered or welded to the contact 604. In some embodiments, a circuit board can include through-hole contacts as described above, and friction fit contacts 604.

To manufacture an implantable device in accordance with one embodiment, interconnect pins 235 are mounted to the implantable device housing 104 such that they are oriented perpendicular to a major surface of the device enclosure housing. A circuit board 204 is placed over the interconnect pins so that through holes on the circuit board align with the interconnect pins and the pins extend through the through holes. A connection can then be made if needed between the connector pins and the circuit board. The housing portions 204, 206 can then be connected together and header 103 can be attached to housing 104 to form pulse generator 105.

In other examples, the header discussed herein can include an antennae and/or electronic components that are used to electrically communicate outside the device.

It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. An implantable device comprising:
a flattened housing having an outer surface including first and second outer major surfaces connected by an outer side wall minor edge surface, wherein the first and second outer major surfaces each have a larger surface area than the outer side wall minor edge surface, the first major surface being parallel to the second major surface;
a circuit board having a plurality of through holes; and
a plurality of interconnect pins within the housing, each of the interconnect pins including a straight shaft oriented perpendicular to the first and second outer major surfaces of the housing;
wherein the circuit board is attached to the interconnect pins such that the pins extend through the through holes of the circuit board.

2. The implantable device of claim 1, wherein at least one of the interconnect pins includes a feedthrough pin oriented such that an outer connection surface of the feedthrough pin lie in a parallel plane to the major surface of the housing.

3. The implantable device of claim 1, wherein the circuit board includes a rigid circuit board.

4. The implantable device of claim 1, wherein the interconnect pins are laid out in a predetermined configuration and the through holes have a matching configuration.

5. The implantable device of claim 1, wherein the circuit board is soldered to the interconnect pins.

6. The implantable device of claim 1, wherein the circuit board is welded, brazed, soldered, or epoxied to the interconnect pins.

7. An implantable device comprising:
a flat electronic assembly housing having an outer surface including two major surfaces connected by a side wall minor surface, wherein the first and second outer major surfaces each have a larger surface area than the outer side wall minor edge surface, wherein the two major surfaces are parallel to each other;
a plurality of feedthrough pins mounted within the electronic assembly housing, each of the plurality of feedthrough pins including a straight shaft oriented perpendicular to the two major surfaces of the electronic assembly housing and such that an outer connection surface of each feedthrough pin lies in a parallel plane to the two major surfaces of the housing; and a circuit board mounted within the electronic assembly housing, the circuit board including a plurality of through holes, wherein the feedthrough pins are electrically connected to the circuit board at the through holes.

8. The implantable device of claim 7, wherein the circuit board includes a rigid circuit board.

9. The implantable device of claim 7, wherein the feedthrough pins are laid out in a predetermined configuration and the through holes have a matching configuration.

10. The implantable device of claim 7, wherein the circuit board is welded, brazed, soldered, or epoxied to the interconnect pins.

11. The implantable device of claim 7, wherein the circuit board is soldered to the interconnect pins.

12. The implantable device of claim 7, wherein the feedthrough pins extend through the through holes of the circuit board.

13. The implantable device of claim 7, wherein the feedthrough pins contact a friction-fit contact on the circuit board.

14. A method comprising:

providing feedthrough pins within a flat implantable device housing, the feedthrough pins being oriented perpendicular to both of a first major surface and a second major outer surface of the device housing, the two major surfaces connected by a side wall minor surface, and the feedthrough pins having an outer connection surface that lies in a parallel plane to both of the first major surface and the second major outer surface of the housing, wherein the first major surface is parallel to the second major surface, and wherein the first and second outer major surfaces each have a larger surface area than the outer side wall minor edge surface;

placing a circuit board having a plurality of through holes over the interconnect pins such that the interconnect pins extend through the through holes; and connecting the interconnect pins to the circuit board at the through holes.

15. The method of claim 14, wherein placing the circuit board includes placing a rigid circuit board.

16. The method of claim 14, including connecting the feedthrough pins to the circuit board by placing the feedthrough pins through through holes on the circuit board, the through holes configured in the same pattern as the feedthrough pins.

17. The method of claim 14, wherein connecting includes welding.

18. The method of claim 14, wherein connecting includes brazing.

19. The method of claim 14, wherein connecting includes soldering.

20. The method of claim 14, wherein connecting includes using conductive epoxy.

21. An implantable device comprising:

a flattened housing having an outer surface including first and second outer major surfaces connected by an outer side wall minor edge surface, wherein the outer side wall minor edge surface defines an outer perimeter surface of the housing extending around the housing between the first outer major surface and the second out major surface, and wherein the first and second outer major surfaces each have a larger surface area than the outer side wall minor edge surface;

a circuit board having a plurality of through holes; and a plurality of interconnect pins within the housing, each of the interconnect pins including a straight shaft oriented perpendicular to the first and second outer major surfaces of the housing;

wherein the circuit board is attached to the interconnect pins such that the pins extend through the through holes of the circuit board.

22. The implantable device of claim 21, wherein the outer side wall surface extends entirely around the housing and separates the first outer major surface from the second outer major surface.

23. The implantable device of claim 21, wherein the first major surface is parallel to the second major surface.

* * * * *

UNITED STATES PATENT AND TRADEMARK OFFICE
CERTIFICATE OF CORRECTION

PATENT NO. : 7,803,014 B2
APPLICATION NO. : 11/278051
DATED : September 28, 2010
INVENTOR(S) : Jason W. Sprain et al.

It is certified that error appears in the above-identified patent and that said Letters Patent is hereby corrected as shown below:

In column 6, line 22, in Claim 21, delete "out" and insert -- outer --, therefor.

Signed and Sealed this

Thirtieth Day of November, 2010

David J. Kappos
*Director of the United States Patent and Trademark Office*